(12) United States Patent
Endrikat et al.

(10) Patent No.: US 8,071,577 B2
(45) Date of Patent: Dec. 6, 2011

(54) MULTI-PHASE CONTRACEPTIVE PREPARATION BASED ON A NATURAL ESTROGEN

(75) Inventors: Jan Endrikat, Kirkland (CA); Bernd Duesterberg, Oberkraemer (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 393 days.

(21) Appl. No.: 11/578,771

(22) PCT Filed: Apr. 15, 2005

(86) PCT No.: PCT/EP2005/004022
§ 371 (c)(1),
(2), (4) Date: Jun. 27, 2007

(87) PCT Pub. No.: WO2005/102247
PCT Pub. Date: Nov. 3, 2005

(65) Prior Publication Data
US 2007/0259840 A1    Nov. 8, 2007

(30) Foreign Application Priority Data
Apr. 20, 2004  (DE) .................... 10 2004 019 743

(51) Int. Cl.
*A61K 31/56* (2006.01)
(52) U.S. Cl. ........................... 514/170; 514/182
(58) Field of Classification Search ................. 514/170, 514/182
See application file for complete search history.

(56) References Cited

U.S. PATENT DOCUMENTS

| | | |
|---|---|---|
| 3,639,600 A | 2/1972 | Hendrix |
| 3,795,734 A | 3/1974 | Rochefort |
| 3,957,982 A | 5/1976 | Lachnit-Fixson et al. |
| 4,066,757 A | 1/1978 | Pasquale |
| 4,272,270 A | 6/1981 | Higgins et al. |
| 4,378,356 A | 3/1983 | DeJager |
| 4,390,531 A | 6/1983 | Edgren |
| 4,530,839 A | 7/1985 | Pasquale |
| 4,544,554 A | 10/1985 | Pasquale |
| 4,616,006 A | 10/1986 | Pasquale |
| 4,621,079 A | 11/1986 | Lachnit-Fixson et al. |
| 4,628,051 A | 12/1986 | Pasquale |
| 4,921,843 A | 5/1990 | Pasquale |
| 5,280,023 A | 1/1994 | Ehrlich et al. |
| 5,583,129 A | 12/1996 | Spona et al. |
| 5,633,242 A | 5/1997 | Oettel et al. |
| 6,027,749 A | 2/2000 | Schmidt-Gollwitzer et al. |
| 6,133,251 A | 10/2000 | Dittgen et al. |
| 6,312,722 B1 | 11/2001 | Schmidt-Gollwitzer et al. |
| 6,670,350 B1 | 12/2003 | Oettel et al. |
| 6,782,282 B2 | 8/2004 | Bielefeldt et al. |
| 6,884,793 B2 | 4/2005 | Dittgen et al. |
| 6,987,101 B1 | 1/2006 | Nashed |
| 2002/0107229 A1 | 8/2002 | Dittgen et al. |
| 2004/0266745 A1 | 12/2004 | Schwanitz et al. |
| 2005/0032756 A1 | 2/2005 | Dittgen et al. |
| 2005/0282790 A1 | 12/2005 | Nashed |
| 2006/0135496 A1 | 6/2006 | DiLiberti et al. |
| 2007/0111977 A1 | 5/2007 | Zeun et al. |
| 2007/0259840 A1 | 11/2007 | Endrikat et al. |
| 2008/0125401 A1 | 5/2008 | Zeun et al. |

FOREIGN PATENT DOCUMENTS

| | | |
|---|---|---|
| BE | 823 689 | 6/1975 |
| CA | 1 090 255 | 11/1980 |
| CA | 2140011 A1 | 1/1994 |
| DE | 2 431 704 | 1/1976 |
| DE | 2 645 307 | 4/1978 |
| DE | 3 341 638 | 5/1984 |
| DE | 3 347 125 | 7/1985 |
| DE | 41 04 385 C1 | 8/1992 |
| DE | 42 24 534 A1 | 1/1994 |
| DE | 43 08 406 C1 | 6/1994 |
| DE | 4 339 934 | 11/1994 |
| DE | 43 13 926 A1 | 11/1994 |
| DE | 4 344 462 | 6/1995 |
| DE | 4 429 374 | 2/1996 |
| DE | 44 29 374 C1 | 2/1996 |
| EP | 26229 | 4/1981 |
| EP | 0 226 679 | 7/1987 |
| EP | 253607 | 1/1988 |
| EP | 0 378 373 A2 | 7/1990 |
| EP | 0 491 415 B1 | 6/1992 |

(Continued)

OTHER PUBLICATIONS

Awward, J. T. et al., "Abnormal uterine bleeding in the perimenopause," Int. J. Fertil., 1993, vol. 38, pp. 261-269.

(Continued)

*Primary Examiner* — San-Ming Hui
(74) *Attorney, Agent, or Firm* — Millen, White, Zelano & Branigan, P.C.

(57) ABSTRACT

The multiphase preparation having higher contraceptive safety and reduced side effects is based on a combination of a natural oestrogen with dienogest or drospirenone. The multiphase preparation is characterized by a first phase consisting of 2 daily dose units of 3 mg of oestradiol valerate, a second phase consisting of 2 groups of daily dose units, wherein a first group is formed by 5 daily dose units each containing a combination of 2 mg of oestradiol valerate and at least two or three times an ovulation-inhibitory dose of dienogest or drospirenone and a second group is formed by 17 daily dose units each containing a combination of 2 mg of oestradiol valerate and at least three or four times the ovulation-inhibitory dose of dienogest or drospirenone, a third phase consisting of 2 daily dose units of 1 mg of oestradiol valerate, and a further phase consisting of 2 daily dose units of pharmaceutically acceptable placebo.

3 Claims, No Drawings

FOREIGN PATENT DOCUMENTS

| | | |
|---|---|---|
| EP | 0 696 454 A2 | 2/1996 |
| EP | 0 770 388 | 5/1997 |
| EP | 0 770 388 A1 | 5/1997 |
| EP | 0 911 029 B1 | 4/2002 |
| EP | 0 835 114 B1 | 5/2003 |
| EP | 1 462 106 | 9/2004 |
| EP | 1 787 649 | 5/2007 |
| NL | 6 911 920 | 2/1970 |
| WO | WO-92 13539 | 8/1992 |
| WO | WO 95/07081 A1 | 3/1995 |
| WO | WO-98 04265 | 2/1998 |
| WO | WO98/04268 * | 2/1998 |
| WO | WO 98/04268 A1 | 2/1998 |
| WO | WO-98 04269 | 2/1998 |
| WO | WO 98/27929 A2 | 7/1998 |
| WO | WO-02 22110 | 3/2002 |
| WO | 2004/112797 | 12/2004 |
| WO | WO 2004/112797 A1 | 12/2004 |
| WO | WO 2005/102247 A2 | 11/2005 |
| WO | WO 2007/002862 A2 | 1/2007 |
| ZA | 8 509 892 | 7/1986 |

OTHER PUBLICATIONS

Speroff et al., "Clinical Gynecologic Endocrinology and infertility," Lippincott, Williams, and Wilkins: Sixth Edition, 1999, pp. 575-593.

Fraser, I. S. et al., "Treatment of Ovulatory and Anovulatory Dysfunctional Uterine Bleeding With Oral Progestogens," Aust. NZ. J. Obetet. Gynaecol., 1990, vol. 30, No. 4, pp. 353-356.

Hickey, M et al., "Progestogens Versus oestrogens and progestogens for irregular uterine bleeding associated with anovulation," The Cochrane Database of Systematic Review, 2000, vol. 1, pp. 1-9.

Steiner, R. et al., "Abnormal Menstrual Bleeding," Schweiz Rundsch. Med. Prax., 2002, vol. 91, pp. 1967-1974.

Opposition filed by Sandoz International GmbH against EP1787649 on Nov. 26, 2009.

English Translation of Opposition filed by Sandoz International GmbH against EP1787649 on Nov. 26, 2009.

Goretzlehner, G. et al., "Zur Nomenklatur der Zyklusstorungen," Frauenarzt, 2005, vol. 46, No. 1, pp. 34-37.

Tapanainen, J. S., "Medical management of menstrual disorders," International Congress Series, 2004, vol. 1266, pp. 63-68.

Golbs, S. et al., "Clinical Findings with the Oral Contraceptive Combination Ethinylestradiol/ Dienogest in Poland," Methods Find Exp Clin Pharmacol, 2002, vol. 24, No. 9, pp. 585-592.

Golbs, S. et al., "Clinical Findings with the Oral Contraceptive Combination Ethinylestradiol/ Dienogest in the Czech Republic," Methods Find Exp. Clin. Pharmacol., vol. 24, No. 10, pp. 689-696.

Mueck, A. O. et al., "Effect on biochemical vasoactive markers during postmenopausal hormone response replacement therapy: estradiol versus estradiol/dienogest," Maturitas, 2001, vol. 38, pp. 305-313.

Kuhl, H. et al., "Aktuelle Entwicklungen in der hormonalen Kontrazeption," Gynakologe, 1992, vol. 25, pp. 231-240.

Watson Pharma, Inc., "About Oral Contraceptives (OCs)," Retrieved from http://www.oralcontraceptives.com/about_benefits.asp on Apr. 5, 2010.

Davis, A. J. et al., "Advances in Contraception," Obstet. Gynecol. Clin. North. Am., Sep. 2000, vol. 27, No. 3, pp. 597-610.

Conrad, J. et al., "Natural Estrogens for Oral Contraception," The Lancet, Sep. 1, 1979, pp. 471.

Moller, Svend E., "Deaths of Infants After Triple Vaccine," The Lancet, Sep. 1, 1979, pp. 472.

Carlborg, Lars, "Comparison of Contraception Acceptability of Levonorgestrel and Ethinyl Oestradiol Administered in one Three-Phasic (Trionetta) and one Monophasic (Neovletta) Version" Contraception, May 1983, vol. 27, No. 5, pp. 439-452.

Guenferich, Peter F., "Oxidation of 17 alpha-Ethynylestradiol by Human Liver Cytochrome p-450," Molecular Pharmacology, vol. 33, pp. 500-508, 1988.

Bocker, R. "In vitro interaction of contraception steroids with human liver cytochrome P-450 enzymes," Department of Toxicology and Pharmacology, University of Erlangen-Nurnberg, pp. 141-148, 1991.

Zhu, Bao Ting et al., "The Carcinogenic Activitiy of Ethinyl Estrogens is Determined by Both Their Hormonal Characteristics and Their Conversion to Catechol Metabolites," Endocrinology, vol. 132, No. 2, 1993, pp. 577-583.

Hirvonen, E. et al., "Oral Contraceptives containing natural estradiol for premenopausal women," Maturitas, 1995, vol. 21, pp. 27-32.

Wenzl, Rene et al., "Ovulation inhibition with a combined oral contraceptive containing 1 mg micronized 17 beta-estradiol," Fertility and Sterility, Oct. 1993, vol. 60, No. 4, pp. 616-619.

Elstein, Max et al., "Studies on Low-dose oral contraceptives: Cervial mucus and plasma hormone changes in relation to circulating d-norgestrel and 17 alpha-ethynyl estradiol concentrations," Fertility and Sterility, Aug. 1976, vol. 27, No. 8, pp. 892-899.

Aktories, K. et al., "Die Beeinflussung des Ovarialzyklus durch verschiedene Typen hormonaler Kontrazeptiva," Geburtsch. U. Frauenheilk, 1976, vol. 36, pp. 318-326.

World Health Organization Task Force on Oral Contraception. A randomized, double-blind study of two combined oral contraceptives containing the same progestogens, but different estrogens. Contraception 1980; 21: 445-59.

Hirvonen, E., et al., A multicenter trial with a new OC using a natural estradiol and cyproterone acetate for women over 35. Adv. Contracept 1990; 6:248.

Kivinen, S., et al., "Efficacy and tolerability of a combined oral contraceptive containing 17 beta-estradiol and desogestrel," Eur. J., Contracept. Reprod. Health Care 1996; 1:183.

Schubert, W., et al., "Ovulation inhibition with 17 beta-estradiol cyclo-octyl acetate and desogestrel," Acta Obstet. Gynecol. Scand. 1987; 66:543-7.

Serup, J., et al., "Natural Oestrogens for Oral Contraception," Lancet 1979; 2:471-2.

Hagstad, A., et al., "Effects of Two Estradiol/Norgestrel Combinations on the Ovulatory Pattern and on Sex Hormone Binding Globulin Capacity in Women around Forty Years of Age," Acta Obstet. Gynecol. Scand. 63: 321-324, 1984.

FDA Approval Letter (with attachments) for NATAZIA®, May 2010, 30 pages.

Hoffmann, H. et al., "Alternatives for the replacement of ethinylestradiol by natural 17 beta-estradiol in dienogest-containing oral contraceptives," Drugs of Today, 1999, vol. 35, pp. 105-113.

Hoffmann, H. et al., "Approaches to the replacement of ethinylestradiol by natural 17 beta-estradiol in combined oral contraceptives," Exp. Toxic Pathol., 1998, vol. 50, pp. 458-464.

Moore, C. et al., "Different alternatives for the substitution of ethylestradiol in oral contraceptives," Jenapharm, 1998, pp. 25-35.

Rees, M., "Estradiol valerate/dienogest," Drugs, 2002, vol. 62, No. 3, pp. 505-506.

Label for Femilar®, "Summary of Product Characterization," (Approved Oct. 28, 1992); Mar. 1, 2011 version—13 pages.

Watson's ANDA letter re: Natazia, Dec. 22, 2010—17 pages.

Clinical Study/Report—Amended, No. AZ94, pp. 2-8, from Endrikat Declaration, of Jan. 21, 2010.

Fruzzetti, F., et al., "Review of clinical experience with estradiol in combined oral contraceptives," Contraceptive 81 (2010) 8-15.

Hirvonen, E., et al., "New natural oestradiol/cyproterone acetate oral contraceptive for pre-menopausal women," Maturitas, 10 (1988) 201-213.

Serup, J., et al., "Effectivity and Acceptability of Oral Contraceptives Containing Natural and Artificial Estrogens in Combination with a Gestagen," Acta Obstet Gynecol Scand 60: 203-206, 1981.

Csemiczky, G., et al., "The Pharmacodynamic Effects of an Oral Contraceptive Containing 3 mg Micronized 17β-Estradiol and 0.150 mg Desogestrel for 21 Days, Followed by 0.030 mg Desogestrel Only for 7 Days," Contraception 1996: 54: 333-338.

Endrikat, J., et al., "A Twelve-Month Comparative Clinical Investigation of Two Low-Dose Oral Contraceptives Containing 20 μg. Ethinylestradiol/75 μg Gestodene and 30 μg Ethinylestradiol/75 μg Gestodene, with Respect to Efficacy, Cycle Control, and Tolerance," Contraception 1997; 55: 131-137.

Endrikat, J., et al, "Multicenter, comparative study of cycle control, efficacy and tolerability of two low-dose oral contraceptives containing 20 μg ethinylestradiol/100 μg levonorgestrel and 20 μg ethinylestradiol/500 μg norethisterone," Contraception 64 (2001) 3-10.

Graser, T., et al., "Comparison of the efficacy and endometrial safety of two estradiol valerate/dienogest combinations and Kliogest® for continuous combined hormone replacement therapy in postmenopausal women," Climacteric 2000: 3: 109-118.

Graser, T., et al., "Dienogest as a Progestin for Hormone Replacement Therapy," Drugs of Today 1999, 35 (Suppl. C): 115-126.

Graser, T., et al., "Effects of a combination of 2 mg estradiol valerate and 3 mg dienogest on coagulation, lipid profile, and glucose metabolism in postmenopausal women," Drugs of Today 2001, 37 (Suppl. G): 87-99.

Graser, T., et al., "Lafamme®: A new oral preparation for continuous combined hormone replacement therapy in postmenopausal woman," Drugs of Today 2001, 37 (Suppl. G): 17-27.

Von Schoultz, B., "Clinical efficacy and safety of combined estradiol valerate and dienogest: a new no-bleed treatment," Climacteric 2003: 6 (Suppl. 2): 24-32.

Wellington, K., et al., "Estradiol Valerate/Dienogest," Drugs 2002: 62 (3): 491-504.

Rudolph, I., et al., "Influence of a continuous combined HRT (2 mg estradiol valerate and 2 mg dienogest) on postmenopausal depression," Climacteric 2004: 7: 301-311, online publication date Sep. 1, 2004, http://www.informaworld.com/smpp/title-content=t713605024.

Astedt, A., et al., "Clinical Trial of a New Oral Contraceptive Pill Containing the Natural Oestrogen 17β-Oestradiol," British J. of Ob. & Gyn., Sep. 1979, vol. 86, pp. 732-736.

Zimmermann, H., et al: "Toxicology of Dienogest" Drugs of Today 1999, 35 (Suppl. C) pp. 13-26 (in English).

Graeser, T., et al: "Dienogest as a Progestin for Hormone . . ." Drugs of Today 1999, 35 (Suppl. C), pp. 115-126 (in English).

C. Moore et al: "Influence of Dienogest on Ovulation in . . ." Clinical Drug Investigation, vol. 18, No. 4, Oct. 1999, pp. 271-278 (in English).

Oettel, M., et al: "The Preclinical and Clinical Profile of Dienogest . . ." Drugs of Today/Medicamentos de Actualidad, J.R. Prous SS.A. Internacional Publishers, ES. vol. 35, 1999, pp. 3-12 (in English).

Strecke, J., et al: "Investigations of the Behaviour of the Vaginal . . ." Z. Versuchstierk, 24, pp. 117-125 (in English), 1982.

Dienogest: Praeklinik un Dklinik Eines Neuen Gestagens By A. Teichmann, Walter de Gruyter Berlin/new York, 1995, p. 101.

P. Rosenbaum et al: "Inhibition of Ovulation be a Novel . . ." The European Journal of Contraception and Reproductive Health Care, 2000; 5, pp. 16-24 (in English).

Taubert et al: "Kotraception Mit Hormonen", 1995, p. 160.

Pierson, R., et al: "Ortho Evra/Evra Versus Oral Contraceptives . . ." Fertility and Sterility, vol. 80, No. 1, Jul. 2003, pp. 34-42 (in English).

Bitzer, J., "Kontrazeption und Sexualität," Therapeutische Umschau, Band 61, 1994 Heft 2, pp. 110-114.

Chuong, C.J., M.D., et al., "Management of abnormal uterine bleeding," Am. J. Obstet. Gynecol., Sep. 1996, pp. 787-792.

Davis, A., M.D., et al., "Triphasic Norgestimate-Ethinyl Estradiol for Treating Dysfunctional Uterine Bleeding," Obstet. & Gynecol., vol. 96, No. 6, Dec. 2000, pp. 913-920, XP-002317447.

Dei, M, et al., "Sex Steroids and Libido," The European Jrnl. of Contraception & Reproductive Health Care, vol. 2 (1997) pp. 253-258.

Durán, M., et al., "Efectividad de estradiol valerato/dienogest en la function sexual durante la menopausia (Estudio Venux)," Acta ginecologica, vol. LXIII, (2006) pp. 1-8.

Endrikat, J., et al., "Ovulation inhibition with four variations of a four-phasic estradiol valerate/dienogest combined oral contraceptive: results of two prospective, randomized, open-label studies," Contraception 78 (2008) pp. 218-225.

Gräser, T., et al., "Continuous-combined treatment of the menopause with combinations of oestradiol valerate and dienogest—a dose-ranging study," Maturitas—The European Menopause Journal, 35 (2000) pp. 253-261, XP-002369505.

Gräser, T., et al., "Dienogest as a Progestin for Hormone Replacement Therapy," Drugs of Today, 1999, 35 (Suppl. C) pp. 115-126, XP-008054769.

Kuhl, H., et al., "Kontrazeption," 2. Völlig neubearbeitete Auflage, 19 Abbildungen, 47 Tabellen—1999 Georg Thieme Verlag, Stuttgart—New York. Cover Page and p. 140, titled 12 Kontrazeption bei Problempatientinnen.

L'Oreal's Application in the Appeal Tribunal Before: Mr. Justice Graham and Mr. Justice Whitford—10th and 23rd Jul. 1970. [No. 20] Dec. 31, 1970 [1970] R.P.C., pp. 565-579.

Moore, C., et al., "Influence of Dienogest on Ovluation in Young Fertile Women," Clinical Pharmacodynamics, Clin. Drug. Invest. 18 (4), Oct. 1999, pp. 271-278, XP-008054770.

Oettel, M., et al., "The Preclinical and Clinical Profile of Dienogest. A Short Overview," Drugs of Today, 1999, 35 (Suppl. C): pp. 3-12, XP-000909647.

Osmanağaoğlu, M.A., et al., "Effect of different preparations of hormone therapy on sexual dysfunction in naturally postmenopausal women," Climacteric, 2006; 9: pp. 464-472.

Rosenbaum, P., et al., "Inhibition of ovulation by a novel progestogen (drospirenone) alone or in combination with ethinylestradiol," The European Journal of Contraception and Reproductive Health Care, 2000; 5: pp. 16-24.

Saletu, B., et al., "Hormone replacement therapy and vigilance Double-blind, placebo-controlled EEG-mapping studies with an estrogen-progestogen combination (Climodien®, Lafamme®) versus estrogen alone in menopausal syndrome patients," Maturitas—The European Menopause Journal, 43 (2002), pp. 165-181.

Timmer, C. J., et al., "Bioequivalence assessment of three different estrdiol formulations in postmenopausal women in an open, randomized, single-dose, 3-way cross-over study," European Journal of Drug Metabolism and Pharmacokinetics, 1999, vol. 24, No. 1, pp. 47-53.

Strecke, V. J., et al., "Untersuchungen zum Verhalten des Vaginalzytogramms bei Beagle-Hündinnen während toxikologischer Langzeituntersuchungen von Gestagenen[1]," Z. Versuchstierk, 24 (1982), pp. 117-125.

Taubert, H.-D., et al., "Kontrazeption mit Hormonen—Ein Leitfaden für die Praxis," 2., überarbeitete und erweiterte Auflage, 79 Abbildungen, 43 Tabellen—1995 Georg Thieme Verlag Stuttgart—New York. . Cover Page and p. 160, titled Hormanale Kontrazeptiva.

Von Schoultz, B., "Clinical efficacy and safety of combined estradiol valerate and dienogest: a new no-bleed treatment," Climacteric, 2003; 6 (Suppl. 2): pp. 24-32, XP-009062446.

Wellington, K., et al., "Estradiol Valerate/Dienogest," Adis New Drug Profile, Drugs, 2002, 62(3)—Abstract, 2 pages.

Wiegratz, I., et al., "Effect of dienogest-containing oral contraceptives on lipid metabolism," Contraception, 65 (2002), pp. 223-229.

Zimmerman, H., et al., "Pharmacokinetics of Estradiol Valerate 2mg + Dienogest 2mg (Climodien® 2/2) after Single and Repeated Oral Administration in Healthy Postmenopausal Women," Clinical Pharmacokinetics, Clin. Drug. Invest., Aug. 20, 2000, (2), Abstract (1 page).

Zimmerman, H., et al., "Toxicology of Dienogest," Drugs of Today, 1999, 35 (Suppl. C): pp. 13-26.

Written Opinion of the International Searching Authority, along with related papers, issued Jul. 25, 2006 in International Application No. PCT/EP2005/004022 (28 pages).

International Search Report issued Aug. 8, 2007 in International Application No. PCT/EP2006/008626 (4 pages).

Written Opinion of the International Searching Authority issued Aug. 8, 2007 in International Application No. PCT/EP2006/008626 (6 pages).

Search Report issued Apr. 30, 2007 in ROC (Taiwan) Patent Application No. 094109222 (1 page).

International Search Report, along with related papers, issued Jan. 4, 2007 in International Application No. PCT/EP2006/009867 (11 pages).

Teichmann, A.T., "Dienogest: Pre-Clinical and clinical results for the new Gestogen," Walter de gruyter, Berlin/New York, p. 101, 1995.

Pierson, R.A., et a l., "Ortho Evar™/Evra™ versus oral contraceptives: follicular development and ovulation in normal cycles and after intentional dosing error," Fertility and Sterility, vol. 80, No. 1, Jul. 2003, pp. 34-42.

Therapeutischer Umschau, 1994;51(2):1-9.

Organon Laboratories Ltd's Application, 1970 (in English).

L'Oreal Application, Dec. 31, 1970 (in English).

Akerlund, M. et al., "Comparative profiles of reliability, cycle control and side effects of two oral contraceptives formulations containing 150uh desogestrel and either 30 ug or 20 ug ethinyl oestradiol," British Journal of Obstetrics and Gynaecology, Sep. 1993, vol. 100, pp. 832-838.

Asche & Co AG C F., "Three-stage combination oral contraceptives—contg. Oestrogen with increasing doses of gestagen," Publication Date. Jan. 22, 1976, English Abstract of DE-2 431 704.

Astedt, B. et al., The natural oestrogenic hormone oestradiol as a new component of combined oral contraceptives, Br Med J, 1977.

Bayer, S. R. et al., "Clinical manifestations and treatment of dysfunctional uterine bleeding," JAMA, Apr. 14, 1993, vol. 269, No. 14.

Clinical Study Report No. A39818, visits from Mar. 2, 2005 to Jul. 20, 2007, Bayer Healthcare.

Darney, P. 1993, Contraception, pp. 323-337.

Darney, P., "Safety and efficacy of a triphasic oral contraceptive containing desogestrel: Results of three multicenter trials," Contraception, Oct. 1993, vol. 48, pp. 323-337.

Darney, P. D. et al., "Contraception-Associated menstrual Problems: Etiology and Managament," Dialogues in Contraception, 1998, vol. 5, No. 5.

Declaration by Maria de las Nieves Fernandez Hernando, Apr. 12, 2001.

Dittgen et al., U.S. Appl. No. 09/648,858, filed Aug. 25, 2000, Amendment dated Dec. 22, 2003, 8 pages.

Dittgen et al., U.S. Appl. No. 09/950,915, filed Sep. 12, 2001, Amendment dated Dec. 18, 2003, 12 pages.

Dittgen et al., U.S. Appl. No. 09/950,915, filed Sep. 12, 2001. Amendment dated Aug. 19, 2004.

Dittgen et al., U.S. Appl. No. 08/738,314, filed Oct. 25, 1996; Declaration filed on Apr. 18, 2000.

Dittgen et al., U.S. Appl. No. 08/738,314, filed Oct. 25, 1996; Amendment dated Jan. 7, 2000, 13 pages.

Drugs of the Future. 2001. vol. 26, No. 6, pp. 577-625.

Endrikat's first declaration U.S. Appl. No. 11/528,771, attached Study 5, 8 pages, submitted Jan. 27, 2010.

Excerpts from U.S. Appl. No. 10/891,729 file history; Reasons for Allowance of Jun. 15, 2009; Amendment of Feb. 13, 2009, Jul. 22, 2008, and Oct. 18, 2004; Official Actions of Nov. 14, 2008 and Apr. 2, 2008; Terminal Disclaimer of Feb. 13, 2009.

Foster, R. H. et al., "Dienogest," Drugs, Nov. 1998, vol. 56, No. 5, pp. 825-833.

Graser, T. et al.. "Organ targeting with the oral progestin dienogest," Drugs of Today, 1996, vol. 32, Suppl. H, pp. 43-55.

Hesslinger Hermann Dr Rer Nat., "Three-phase product for contraception composed of ethinylestradiol and lynestrenol," Data Retrieved from Espacenet Database, Publication Date May 3, 1984; English Abstract of DE 3 341 638.

Hoffmann et al., Pharmakokinetik von Dienogest als monopraparat und in kombination mit ethinylestradiol. dienogest—praklinik und klinik eines gestagens, 2. Auflage, Herausgegeben von A. T. Teichmann, Walter de Gruyter, Berlin/New York, 1995. pp. 95-104.

Kwiecien, M. et al., "Bleeding patterns and patient acceptability of standard or continous dosing regimens of a low dose oral contraceptive: a randomized trial," Contraception, 2003, vol. 67, pp. 9-13.

Lox, C. D. et al., "Biochemical effects in women following one year's exposure to a new triphasic contraceptive—I. Chemistry Profiles," Gen. Pharmac., 1996, vol. 27, No. 2, pp. 367-370.

Miller et al., "Continuous combination oral contraceptives pills to eliminate withdrawal bleeding: A randomized trial," Obstetrics and Gynecology, Apr. 2003, vol. 101. No. 4, pp. 653-661.

Moore, C. et al., "Der Einfluss von Dienogest auf die Ovulation junger Frauen und auf ausgewahlte endokrinologische Parameter." Dienogest: Praklinik und Klinik . . . 1995, pp. 161-170.

Package Insert Climodien. Mar. 23, 2006.

Public Assessment Report of the Medicines Evaluation Board, Qlaira, 2009.

Rosenbaum, P. et al., "Inhibition of ovulation by a novel progestogen (drospirenone) alone of in combination with ethinylestradiol," European Journal of Contraception and Reproductive Health Care. 2005, vol. 5, pp. 16-24.

Schwarz, B. E. et al., "Reference period analysis of vaginal bleeding with triphasic oral contraceptive agents containing norethindrone of levonorgestrel: a comparison study," Int. J Fertility, 1992, vol. 37, No. 3, pp. 176-182.

Sheth, A. et al., "Task Force on Oral Contraceptives," Contraception, 1982, vol. 25, No. 3. pp. 243-252.

Taubert, H. D. et al., Kontrazeption mit Hormonen. 1995 pp. 397-398.

Taubert, H. et al., Kontazeption mit Hormonen. 1995, pp. 125-128.

Taubert, H. et al., Kontazeption mit Hormonen. 1995, pp. 61-62.

Teichmann, A. et al., "Pharmacology of estradiol valerate/dienogest" Climacteric, 2003, vol. 6, Suppl. 2. pp. 17-23.

Tuimala, T. et al., "A clinical comparison in finland of two oral contraceptives containing 0 150 mg Desogestrel in combination with 0.020mg or 0 030 mg Ethinylestradiol." Acta Obstet Gynecol Scand Suppl., 1987, vol. 144, pp. 7-12.

Udoff et al., "Combined continuous hormone replacement therapy: A critical review." Obstetrics & Gynecology, Aug. 1995, vol. 86. No. 2.

Umbreit Klause Dr Med., "Ovulation-inhibiting composition for hormonal contraception," Data Retrieved from the Espacenet Database, Publication Date Nov. 10, 1994, English Abstract of DE 4 339 934.

Unisearch Ltd., "Sequential oral contraceptive pack," Publication Date: Feb. 9. 1970; English Abstract of NL-6 911 920.

Wiegratz, I. et al., "Effect of four different oral contraceptives on various sex hormones and serum-binding globulins," Contraception, 2003 vol. 67, pp. 25-32.

Wright, J. V. et al., Comparative Measurements of Serum Estriol, Estradiol, and Estrone in Non-pregnant, Premenopausal Women: A Preliminary Investigation, Altern Med Rev. (U.S.), Aug. 1999, vol. 4, No. 4, pp. 266-270.

Zimmermann, T. et al., "The efficacy and tolerability of Valette: a postmarketing surveillance study," Eur J. Contracept. Reprod. Health Care, Sep. 1999. vol. 4 No. 3, pp. 155-164.

* cited by examiner

MULTI-PHASE CONTRACEPTIVE PREPARATION BASED ON A NATURAL ESTROGEN

BACKGROUND OF THE INVENTION

1. The Field of the Invention

The invention relates to a multiphase product for contraception based on a natural oestrogen with a synthetic progestogen.

Compared with the generic conventional ovulation-inhibiting products which have proved to be reliable and safe on wide use for a long time, this multiphase product achieves a greater contraceptive reliability over the entire duration of the cycle, improves the cyclic bleeding behaviour and minimizes or eliminates side effects such as breast tenderness, headaches, depressive moods and libido changes and the like.

2. Related Art

The patent literature discloses multiphase products based on natural oestrogens in combination with progestogens.

The patent EP 0 770 388 B1 describes a multiphase product for contraception whose first phase consists of 2 to 4 daily dose units, and each daily dose unit contains as active ingredient exclusively natural oestrogens. The second phase of the multiphase product consists of 2 groups of daily dose units with a combination of at least one natural oestrogen and at least one synthetic or natural progestogen. In this case, the first group is formed by 5 to 3 daily dose units and the second group is formed by 17 to 13 daily dose units. A third phase consists of 2 to 4 daily dose units, and each daily dose unit contains as active ingredient exclusively natural oestrogens. The daily dose unit of natural oestrogen remains constant within the phases, but falls from phase 1 to phase 3. The proportion of synthetic or natural progestogen in the second group of the second phase exceeds the proportion in the first group. A final phase consists of 2 to 4 daily dose units, and each daily dose unit contains as active ingredient a pharmaceutically acceptable placebo.

Use example 5 indicates a combination of oestradiol valerate with dienogest. In this case, in the first phase 3 daily dose units of 3 mg of oestradiol valerate, in the second phase, in the first group, 4 daily dose units of 2 mg of oestradiol valerate plus 1 mg of dienogest, in the second group of this second phase 16 daily dose units of 2 mg of oestradiol valerate plus 2 mg of dienogest and in the third phase 2 daily dose units of 1 mg of oestradiol valerate are administered. The last phase contains 3 daily dose units of pharmaceutically acceptable placebo.

It is additionally known that the contraceptive reliability of combination products derives from the effect of both components, of the oestrogen and of the progestogen.

It is also known that the ovulation-inhibitory dose requires 1.0 mg a day for dienogest—Dienogest: Präklinik und Klinik eines neuen Gestagens, edited by A. T. Teichmann, Walter de Gruyter Berlin/New York (1995), p. 101) and 2.0-3.0 mg for drospirenone (Rosenbaum P, Schmidt W, Helmerhorst F M et al., Inhibition of ovulation by a novel progestogen (drospirenone) . . . , Eur contracept. Reprod. Health Care 5: 16-24 (2000)).

Moreover, TAUBERT, H.-D. and KUHL, H. (Kontrazeption mit Hormonen, editors Taubert, H.-D. et al., Georg Thieme Verlag Stuttgart/New York (1995), p. 160) show that there is no connection whatsoever between the occurrence of irregular bleeding and low serum concentrations of the oestrogen, in this case ethinyl-oestradiol, or of the particular progestogen.

SUMMARY OF THE INVENTION

It is consequently an object of the invention to provide a composition for hormonal contraception based on a natural oestrogen which, compared with the generic conventional ovulation-inhibiting compositions based on natural oestrogens, achieves a greater contraceptive reliability over the entire duration of the cycle, improves the cyclic bleeding behaviour, and controls side effects such as breast tenderness, headaches, depressive moods and libido changes and the like. This object is achieved according to the invention by a multiphase product for contraception, whose first phase consists of 2 daily dose units of 3 mg of oestradiol valerate. A second phase consists of 2 groups of daily dose units, where a first group contains 5 daily dose units each consisting of a combination of 2 mg of oestradiol valerate and at least two or three times the ovulation-inhibitory dose of a synthetic progestogen. The second group of the second phase consists of 17 daily dose units each consisting of a combination of 2 mg of oestradiol valerate and at least three or four times the ovulation inhibitory does of a synthetic progestogen. A third phase contains 2 daily dose units of 1 mg of oestradiol valerate and a further phase of 2 daily dose units of pharmaceutically acceptable placebo.

It is advantageously possible to employ as synthetic progestational active ingredient dienogest, drospirenone or a progestogen with at least twice its known ovulation-inhibitory dose. It is also possible to employ as progestational active ingredients substances of the 19-nortestosterone derivatives such as levonorgestrel, gestodene, norgestimate, desogestrel and norethisterone and its derivatives such as norethisterone acetate and norethisterone enanthate, and substances of the C-21-progestogens such as chlormadinone acetate, cyproterone acetate and medroxyprogesterone acetate.

The multiphase product according to the invention is particularly suitable for oral administration, but intravaginal, parenteral, including topical, rectal, intranasal, intrabuccal or sublingual administrations are also conceivable as dosage forms.

The multiphase product is produced with the conventional solid or liquid carriers or diluents and the excipients conventionally used in pharmaceutical technology appropriate for the desired mode of administration with a suitable dosage in a known manner.

Tablets, film-coated tablets, sugar-coated tablets or hard gelatin capsules are preferably used for oral administration.

EXEMPLARY EMBODIMENTS

The invention is to be demonstrated by some examples of use. In this connection, in particular the contraceptive reliability, the cyclic bleeding behaviour of the woman, and the tolerability of the administration regimen is demonstrated.

Contraceptive Reliability

The contraceptive reliability was demonstrated in principle by determining the Hoogland score which uses the follicle size, the oestradiol level and progesterone values. In the present case, the progesterone serum concentration was measured radio-immunologically on selected days of the cycle, and the number of ovulations (Hoogland score 6) and of luteinized, non-ruptured follicles (Hoogland score 5) was determined.

Cycle Stability

The cycle stability was assessed on the basis of a bleeding pattern recorded for each cycle. Of particular interest in this connection was the occurrence of irregular bleeding (spotting or breakthrough bleeding). The mode of recording was standardized. The data were analysed descriptively.

Tolerability

The tolerability was tested on the basis of subjective feelings such as headaches, depressive moods, breast tenderness, gastric upsets (nausea/vomiting), oedemas and libido changes.

Use Example 1

The following regimen is used:

| days 1 to 2 | 3 mg of oestradiol valerate/d |
| days 3 to 7 | 2 mg of oestradiol valerate/d + 2 mg of dienogest/d |
| days 8 to 24 | 2 mg of oestradiol valerate/d + 3 mg of dienogest/d |
| days 25 to 26 | 1 mg of oestradiol valerate/d |
| days 27 to 28 | placebo |

The study is carried out on 93 female subjects 18 to 35 years old. The duration of intake amounts to 3 cycles in each case, with only cycles 2 and 3 being observed.

In the $2^{nd}$ cycle (primary target variable), 3 of 93 women (3.28%) ovulate, and 2 of 92 women in the $3^{rd}$ cycle.

It is thus possible to record reliable inhibition of ovulation in 96.77% on use of the administration regimen according to the invention.

At the same time, good tolerability is found on intake of the administration regimen according to the invention.

Use Example 2

| days 1 to 2 | 3 mg of oestradiol valerate/d |
| days 3 to 7 | 2 mg of oestradiol valerate/d + 3 mg of dienogest/d |
| days 8 to 24 | 2 mg of oestradiol valerate/d + 4 mg of dienogest/d |
| days 25 to 26 | 1 mg of oestradiol valerate/d |
| days 27 to 28 | placebo |

The study is carried out on 93 female subjects 18 to 35 years old. The duration of intake amounts to 3 cycles in each case, with only cycles 2 and 3 being observed.

In the $2^{nd}$ cycle (primary target variable), 2 of 93 women (2.15%) ovulate, and 2 of 92 women in the $3^{rd}$ cycle.

It is thus possible to record reliable inhibition of ovulation in 97.85% on use of the administration regimen according to the invention.

At the same time, good tolerability is found on intake of the administration regimen according to the invention.

It is possible with the two use examples to record an adequate inhibition of ovulation of respectively 97.85% and 96.77%. Very recent investigations with conventional ovulation inhibitors by Pierson R A et al., "Ortho Evra/Evra versus oral contraceptives: follicular development...", Fertil. Steril. 80(1), pp. 34-42 (2003) demonstrate ovulation in a certain percentage even with products which have proved to be reliable and safe on wide use for a long time. In the second treatment cycle it was possible to observe ovulations for example with a three-phase levonorgestrel-containing oral contraceptive in 14% (3 of 22), with a monophasic levonorgestrel-containing oral contraceptive (6 of 25) and with a triphasic norgestimate-containing oral contraceptive in 16% (4 of 25). These values are distinctly above those for the products according to the invention, so that a higher reliability can be expected with these compared with Pierson et al.

The invention claimed is:

1. A multiphase product for contraception comprising:
   a first phase of 2 daily dosage units, each comprising 3 mg of estradiol valerate,
   a second phase of 2 groups of daily dosage units, a first group comprising 5 daily dosage units, each of which comprises 2 mg of estradiol valerate and 2 mg of dienogest, and a second group comprising 17 daily dosage units, each of which comprises 2 mg of estradiol valerate and 3 mg of dienogest;
   a third phase of 2 two daily dosage units, each comprising 1 mg of estradiol valerate, and
   a fourth phase of 2 two daily dosage units, each comprising a pharmaceutically acceptable placebo.

2. A multiphase oral contraception product comprising:
   a first phase of 2 daily oral dosage units, each comprising 3 mg of estradiol valerate,
   a second phase of 2 groups of daily oral dosage units, a first group comprising 5 daily oral dosage units, each of which comprises 2 mg of estradiol valerate and 2 mg of dienogest, and a second group comprising 17 daily oral dosage units, each of which comprises 2 mg of estradiol valerate and 3 mg of dienogest;
   a third phase of 2 daily oral dosage units, each comprising 1 mg of estradiol valerate, and
   a fourth phase of 2 daily oral dosage units, each comprising a pharmaceutically acceptable placebo.

3. A method of oral contraception comprising orally administering to a woman:
   one oral dosage unit comprising 3 mg of estradiol valerate daily for 2 days,
   then one oral dosage unit comprising 2 mg of estradiol valerate and 2 mg of dienogest daily for 5 days,
   then one oral dosage unit comprising 2 mg of estradiol valerate and 3 mg of dienogest daily for 17 days,
   then one oral dosage unit comprising 1 mg of estradiol valerate daily for 2 days, and
   then one oral dosage unit comprising a pharmaceutically acceptable placebo daily for 2 days.

* * * * *